United States Patent [19]

Hiltebrandt

[11] 4,362,160
[45] Dec. 7, 1982

[54] ENDOSCOPES

[75] Inventor: Siegfried Hiltebrandt, Knittlingen, Fed. Rep. of Germany

[73] Assignee: Richard Wolf GmbH, Knittlingen, Fed. Rep. of Germany

[21] Appl. No.: 169,610

[22] Filed: Jul. 17, 1980

[30] Foreign Application Priority Data

Jul. 24, 1979 [DE] Fed. Rep. of Germany ... 7921081[U]

[51] Int. Cl.³ ............................................ A61B 17/32
[52] U.S. Cl. ......................... 128/303.15; 128/303.17
[58] Field of Search ............. 128/4, 6, 303.14, 303.15, 128/303.16, 303.17, 305

[56] References Cited

U.S. PATENT DOCUMENTS 3,175,554 3/1965 Stewart ................................ 128/754
3,336,916 8/1967 Edlich ......................... 128/303.17 X
4,116,198 9/1978 Roos ................................ 128/303.15
4,149,538 4/1979 Mrava et al. ................... 128/303.15
4,203,444 5/1980 Bonnell et al. ................. 128/305 X Primary Examiner—Gene Mancene
Assistant Examiner—Robert P. Swiatek
Attorney, Agent, or Firm—Kinzer, Plyer, Dorn & McEachran

[57] ABSTRACT

An endoscope, particularly for coagulating or resectioning parts of the cartilage of the meniscus of the knee joint under application of a unipolar HF loop electrode that has a supply lead which extends, together with an optical system, through an endoscope tube for proximal connection to an HF generator. The endoscope tube is electrically insulated externally and is provided at its distal end with excisions at either side of its vertical axial plane to form apertures and a stem delimiting the electrode loop at the distal end is situated in the vertical axial plane in the area of the excisions within the tube.

4 Claims, 8 Drawing Figures

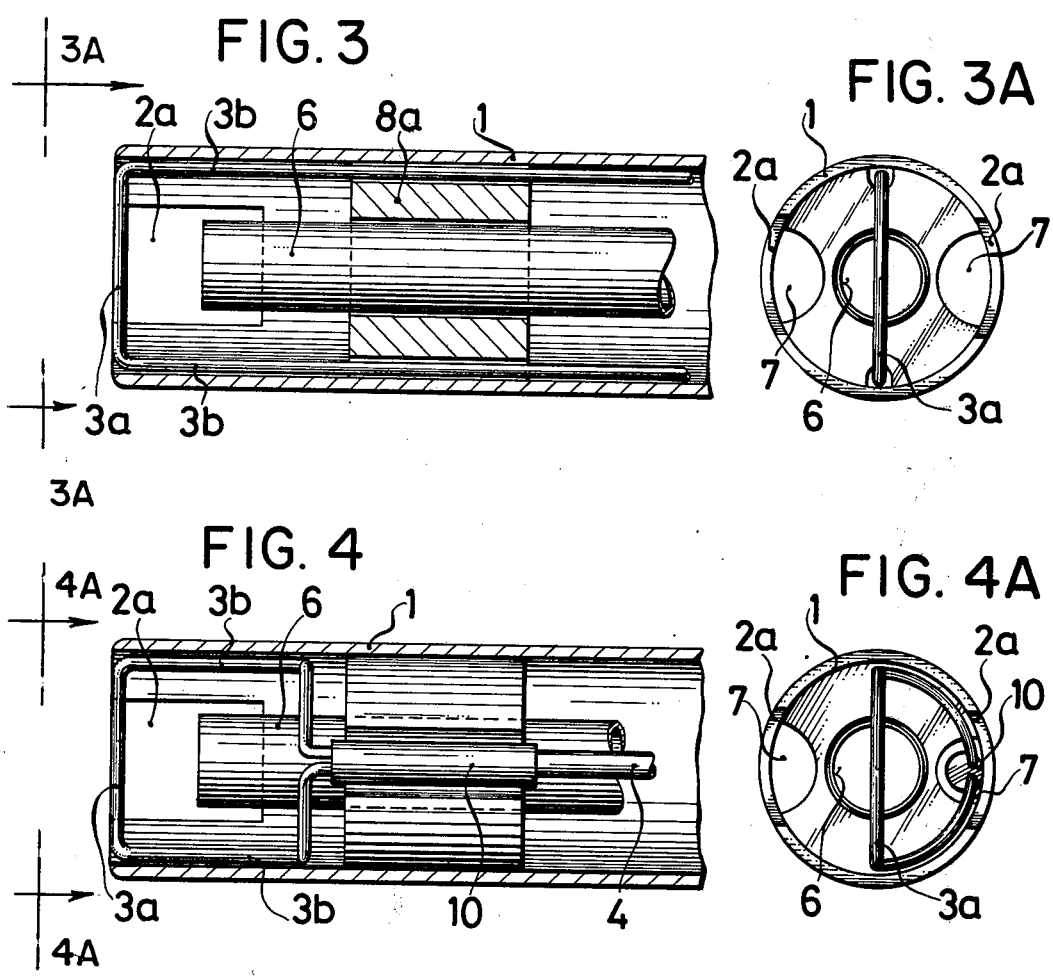

ENDOSCOPES

BACKGROUND OF THE INVENTION

The present invention relates to endoscopes, particularly for coagulating or resectioning parts of the cartilage of the meniscus of the knee joint under application of a unipolar HF loop electrode that has a supply lead which extends, together with an optical system, through an endoscope tube for proximal connection to an HF generator.

Injuries are frequently incurred during sporting events in the area of the knee joint, in particular to the menisci, in the form of longitudinal cracks or of cracks in the anterior or posterior projection.

It is an object of the invention to reduce the enlargement of injuries in the knee joint, in particular the enlargement of the aforesaid meniscus cracks, and the pains caused by the injury, and to remove fissured and fringed cartilage parts of the meniscus by coagulation or resection, under observation.

SUMMARY OF THE INVENTION

Accordingly, the invention consists in an endoscope, particularly for coagulating or resectioning parts of the cartilage of the meniscus of the knee joint under application of a unipolar HF loop electrode that has a supply lead which extends, together with an optical system, through an endoscope tube for proximal connection to an HF generator, wherein said endoscope tube is electrically insulated externally and is provided at its distal end with excisions at either side of its vertical axial plane to form apertures and wherein a stem delimiting said electrode loop at the distal end is situated in said vertical axial plane in the projected area of said excisions within said tube.

The two distal tube excisions advantageously have the form of a triangle or a rectangle, in side view.

Due to the construction according to the invention, the doctor administering the patient's treatment may penetrate horizontally into the space between the two joint surfaces of a knee joint which are to be spread apart and may enflank or capture the fissured or fringed parts of the meniscus with the mouth-like excisions at the distal sides of the endoscope tube, these excisions being approximately matched to the outline of the cross-sectionally wedge-shaped menicus thereby better to deal with injuries to the latter. In doing so, it is possible by means of the loop electrode to remove the fissured or fringed cartilage parts of the meniscus by coagulation or resection, while adjacently situated joint sections or tissue sections are protected by the insulating tube.

It may be necessary in some cases to move the HF loop electrode a little out of the distal end of the tube, so that parts may also be coagulated which cannot be enflanked by the mouth-like excisions. An endoscope according to the invention may alternatively have excised (cut out) apertures differing from the triangular at the distal end of the tube, to secure adaptation to other contours of the parts which are to be treated by coagulation.

BRIEF DESCRIPTION OF THE DRAWINGS

In order that the invention may be more clearly understood, reference will now be made to the accompanying drawings which show certain embodiments thereof by way of example and in which:

FIGS. 2 to 4 severally show the distal portions of other embodiments of the endoscope in vertical axial cross-section; and FIGS. 1A through 4A show end views of FIGS. 1 through 4, respectively.

DETAILED DESCRIPTION OF PREFERRED EMBODIMENTS

Figure 1:
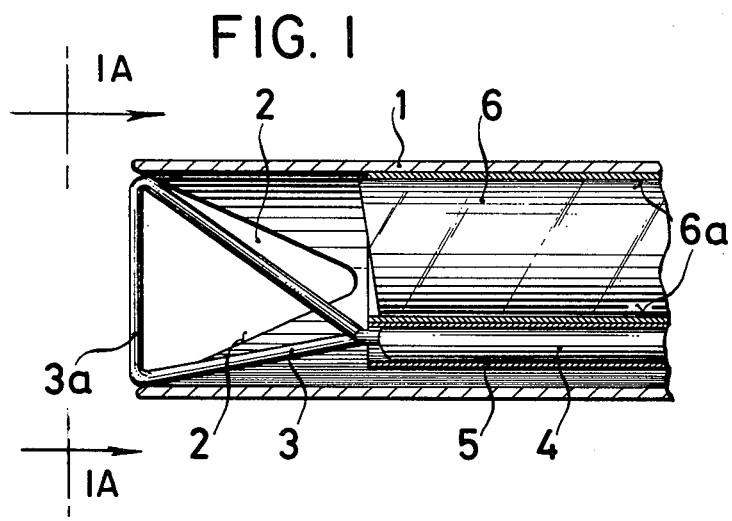
FIG. 1 shows the distal portion of a first embodiment in axial section.
Figure 1A:
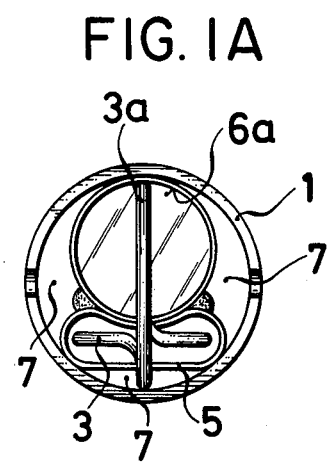

Referring now to the drawings, the endoscope shown in FIG. 1 comprises a tube 1 of insulating material or of metal having an external insulation. At the distal end, the opposing sides of the tube 1 are provided with mouth-like excisions 2, which in sideview correspond to the triangular or wedge-shaped outline of the meniscus in the human knee joint.

An HF coagulation loop or resection loop 3 having a straight vertical terminal stem 3a located in the vertical axial plane, corresponds in outline approximately to the mouth-like excision 2, and is situated in the distal portion of the tube in the area of this mouth-like excision 2. This loop 3, 3a may be connected via a proximal supply lead 4 to the one terminal of an HF current source whose other terminal is connected to an electrode which is to be placed on a substantial area of the body. The supply lead 4 passes through a guide tube 5 which is firmly joined to the guide tube 6a of an optical system 6 which extends off-centre through the endoscope tube 1. The optical system guide tube 6a, the guide tube 5 and the endoscope tube 1 are joined together proximally by a tapered proximal handle (not shown) which engages in a tapered recess of the tube 1. The coagulation loop 3, 3a may be displaced axially out of the tube 1 with the supply lead 4, by means of this proximal handle.

The spaces 7 between the tube 1, the guide 5 and the optical system 6 may be utilised for flushing the knee joint space and for drawing off portions of resectioned cartilage and flushing liquid.

After the knee joint surfaces have been spread apart, the distal end of the endoscope tube 1 is moved up to the damaged spot of a meniscus, and the loop 3, 3a is connected to the HF current source, so that the fissured place and/or frayed out parts may be coagulated or resectioned, the mouthlike excision 2 enflanking the meniscus partly or even wholly, depending on the depth of the injury. Beyond the coagulating or resectioning operation on the injury to the meniscus, other joint elements and/or tissue sections within the knee joint in the area of the mouth like excision are adequately protected by the insulated distal portions of the tube 1.

Figure 2:
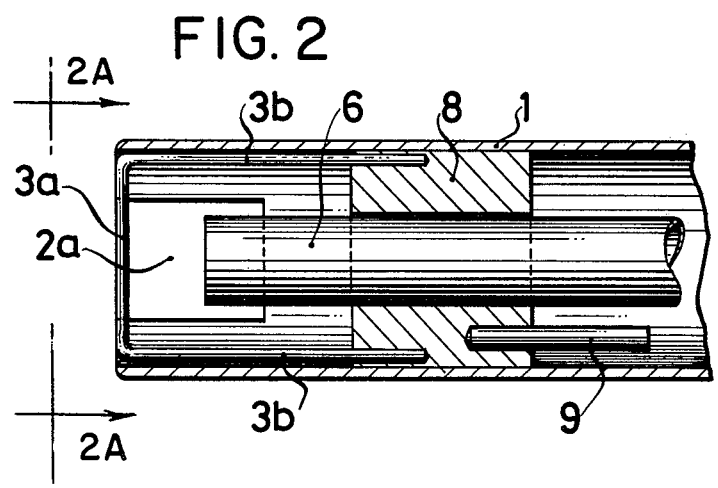
Figure 2A:
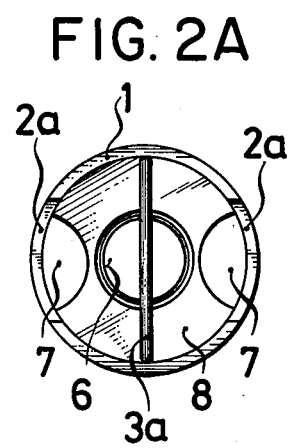

In the embodiments shown in FIGS. 2 to 4, in which parts corresponding to those in FIG. 1 are marked with identical reference symbols, the ambilateral distal excisions 2a of the endoscope tube 1 are rectangular e.g. for adaptation to the outline of other damaged cartilage or tissue parts which are to be resectioned.

In the embodiment of FIG. 2, the cutting or coagulating loop comprises a loop stem 3a and loop limbs 3b which are secured in a slider 8, which is traversed centrally by the optical system 6, and which may be displaced along the optical system 6 together with the loop by means of an axially displaceable rod 9 acting as a current supply line. The passages 7 again serve the purpose of feeding in and drawing off scavenging or flushing liquid.

In the embodiment of FIG. 3, the limbs 3b of the cutting or coagulating loop are led through a stationary element 8a in such manner that they may be displaced freely towards the proximal extremity and may be connected to the one terminal of an HF current source, these limbs again being arranged to be axially displaceable in such manner that the loop 3a 3b may be moved a little out of the distal end of the shaft.

In the embodiment of FIG. 4, the limbs 3b of the cutting loop are joined together at 10 by a sheath member 4 which may be connected to a terminal of the HF generator.

It will be apparent that the installation and connection of the cutting loop 3 to the HF current generator as shown in FIGS. 2 to 4 may also be applied to the embodiment shown in FIG. 1.

A unipolar coagulation or resection of injuries to cartilage and tissue elements is possible in all cases, primarily in the knee joint, the cartilage or tissue elements situated beyond the injured parts which are to be resectioned, being protected by the distal end of the insulating tube in the area of the excision 2, 2a.

I claim:
1. An endoscope for coagulating or resectioning damaged parts of the cartilage of the meniscus of the knee joint under application of a unipolar HF loop electrode that has a supply lead which extends, together with an optical system, through an endoscope tube for proximal connection to an HF generator, wherein said endoscope tube is electrically insulated to prevent injury to adjacent areas of the knee joint anatomy and is provided at its distal end with distal delimiting excisions at either side of its vertical axial plane to form apertures in the sides of the tube for enflanking the damaged cartilage, said excisions having a geometry corresponding nearly to the cartilage to be enflanked, and wherein a stem delimiting said electrode loop at the distal end is situated in said vertical axial plane in the protected area of and between said excisions at the distal end of said tube.

2. An endoscope according to claim 1, wherein said distal excisions are triangular in side view.

3. An endoscope according to claim 1, wherein said distal excisions are rectangular in side view.

4. An endoscope according to claim 1 wherein said electrode loop is axially displaceable out of said tube.

* * * * *